United States Patent
Ooike et al.

(10) Patent No.: US 6,231,740 B1
(45) Date of Patent: May 15, 2001

(54) ELECTROPHORESIS APPARATUS HAVING AN ELECTRIC CONTROLLER

(75) Inventors: Akio Ooike, Komoro; Kouichi Kudo, Saku; Eizo Sugimoto, Tokyo; Masato Murakami, Kashiwa; Hiromu Ishibashi, Tokyo, all of (JP)

(73) Assignees: Cosmo Bio Co., Ltd.; Advance Co., Ltd., both of (JP)

( * ) Notice: Subject to any disclaimer, the term of this patent is extended or adjusted under 35 U.S.C. 154(b) by 0 days.

(21) Appl. No.: 09/315,607

(22) Filed: May 20, 1999

Related U.S. Application Data

(62) Division of application No. 08/871,228, filed on Jun. 9, 1997, now abandoned.

(30) Foreign Application Priority Data

Jul. 18, 1996 (JP) .................................................. 8-206409

(51) Int. Cl.⁷ .................................................. G01N 27/26
(52) U.S. Cl. .......................................... 204/606; 204/600
(58) Field of Search .................................. 204/600, 601, 204/602, 606, 607

(56) References Cited

U.S. PATENT DOCUMENTS 3,906,293 * 9/1975 Meshbane et al. ..................... 361/42
5,055,172 * 10/1991 Cathel et al. ........................ 204/608

* cited by examiner

Primary Examiner—T. Tung
Assistant Examiner—Alex Noguerola
(74) Attorney, Agent, or Firm—McGlew & Tuttle, P.C.

(57) ABSTRACT

A simplified electrophoresis apparatus which imposes no excessive operating burden on users, permits stable control, can be configured compact and light in weight, and allows electrophoresis to be carried out as excellently as the conventional electrophoresis apparatus. The electrophoresis apparatus comprises rectifier means (A) which rectifies an AC current from a universal AC power source and outputs a rectified wave, an electrophoresis cell and an electric controller which applies an electric output from said rectifier means (A) to a carrier disposed in the electrophoresis cell, the electric controller comprising control means (3) for indirectly controlling, in accordance with external inputs, a driving section (6) which controls an electric output from the rectifier circuit.

19 Claims, 4 Drawing Sheets

Fig. 3
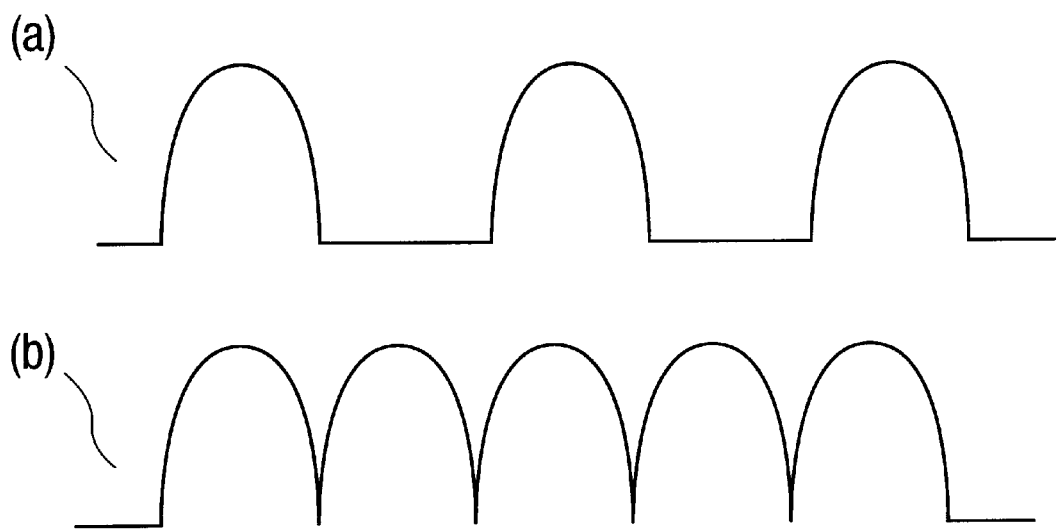
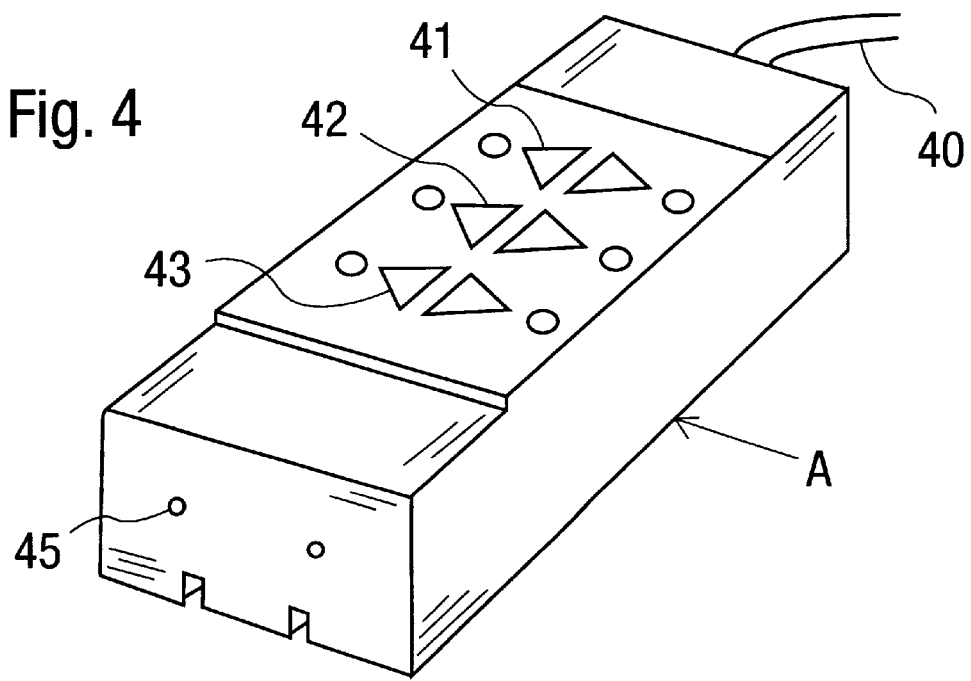
Fig. 4

ELECTROPHORESIS APPARATUS HAVING AN ELECTRIC CONTROLLER

This is a divisional of application Ser. No. 08/871,228 filed Jun. 9, 1997, now abandoned, and the entire disclosure of this prior application is considered to be part of the disclosure of the accompanying application and is hereby incorporated by reference therein.

TECHNICAL FIELD

The present invention relates to a simplified electrophoresis apparatus which is used for fixing, retrieving and refining samples extracted from living bodies in analyses of DNAs and proteins by the electrophoresis which is widely utilized as a basic technique for molecular biology, biochemistry and clinical chemistry.

BACKGROUND ART

An electrophoresis apparatus disclosed by Japanese Utility Model Application Laid-Open No. 63-39639 is known as a conventional simplified electrophoresis apparatus. This electrophoresis apparatus is composed only of fuses, rectifier means and, switches which are used for starting and stopping operations and changing output waveforms, and is capable of supplying an electric current in accordance with impedance of an electrophoresis carrier.

However, the electrophoresis apparatus disclosed by the invention mentioned above is connected directly to a universal AC power source such as a domestic AC 100 V power source and may possibly allow an electric current having a large capacity to be supplied when impedance of an electrophoresis carrier is abruptly lowered or a member of the electrophoresis apparatus is shorted.

Though an electric current having such a large capacity is remarkably hazardous to human bodies, the electrophoresis apparatus provides electric insulation only by breakage of built-in fuses and a protective function of a casing which accommodates electronic circuits. Accordingly, users must always pay attentions to deterioration of mechanical structure of switching means caused due to frequent operations or long-term use and adhesion of splashed electrophoretic gels to the operating switches. Speaking of an electric current allowed for the fuse, on the other hand, the electrophoresis apparatus restricts circuit currents only within a limit since it must allow electric currents required for experiments, thereby requiring elaborate cares for handling and posing extremely serious problems for practical use.

DISCLOSURE OF THE INVENTION

It is therefore a primary object of the present invention to provide a simplified electrophoresis apparatus which can be operated stably without imposing excessive burdens on users, configured compact and light in weight, and carry out electrophoresis as excellently as the conventional apparatus.

For accomplishing this object, the simplified electrophoresis apparatus according to the present invention is configured as an apparatus which comprises rectifier means for rectifying and outputting an AC current from a universal AC power source, an electrophoresis cell, and an electric controller for applying an electric output from the rectifier circuits to a carrier disposed in the electrophoresis cell, wherein the electric controller comprises control means capable of indirectly controlling a driving section which controls the electric output from the rectifier circuit in accordance with external inupts so as to constitute a safe interface which allows electrophoresis to be carried out as desired with less deterioration of the driving section which directly controls electrophoresis outputs so that the electrophoresis apparatus can be used stably.

Speaking of a structure of the simplified electrophoresis apparatus according to the present invention, the electric controller is configured so that it cannot be connected or energized so long as the electrophoresis cell is not protected with a cover, and the cover for the electrophoresis cell is configured so as to have a semicylindrical or semispherical surface for preventing water drops from adhering to an observation surface located on a top surface of the cover to facilitate observation and a ventilation structure having ventilation holes formed in the cover for preventing it from being dimmed.

BRIEF DESCRIPTION OF THE DRAWINGS

FIGS. 3a and 3b are diagrams illustrating rectified waveforms;

FIG. 4 is a perspective view illustrating an electric controller;

BEST MODE FOR CARRYING OUT THE INVENTION

Figure 1:
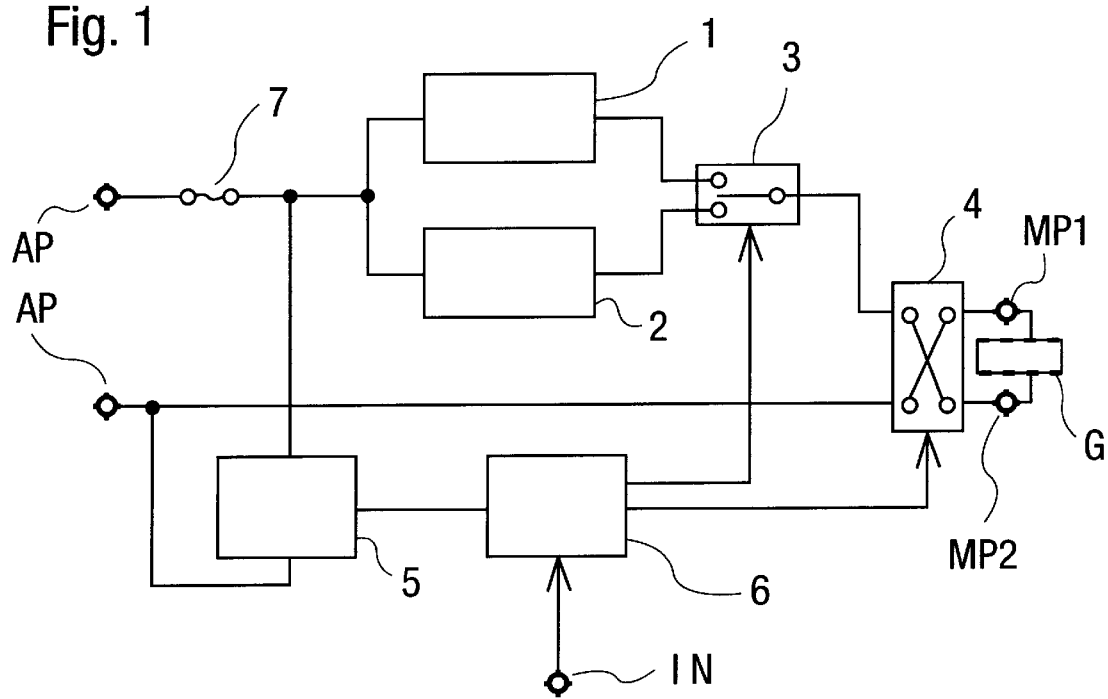
FIG. 1 is a block diagram illustrating an embodiment of the simplified electrophoresis apparatus according to the present invention.

An electric controller according to the present invention will be described with reference to FIG. 1.

As rectifier circuits, a half-wave rectified wave generator 1 and a full-wave rectified wave generator 2 are composed of diodes and diode bridges.

These two rectified wave generators are connected to a change-over switch 3 so that the rectified wave generators can be switched by external inputs. The change-over switch 3 is composed, for example, of a relay, an EFT, a transistor or a combination thereof. As a switching element, a relay is preferable since it has a low resistance when it is turned on and high insulating property.

An output of the switch 3 is connected to the polarity switching relay 4 so that it is changed over like the switch 3 according to an external input.

A signal for driving the change-over switch 3 and the polarity switching relay 4 is driven by input means 6 which outputs a switch driving signal corresponding to a manual control activated by control means 5 for outputting a DC voltage converted from a universal AC voltage for driving a low voltage type driving elements such as a low voltage IC and an external input IN such as a signal transmitted by way of a transmitting medium such as radio waves or infrared rays.

A reference numeral 7 represents switching means, such as a fuse which is blown off for protecting the circuits and an operator in occurrence of an overcurrent, etc. A reusable element such as a small circuit breaker may be used on place of the fuse which is not reusable.

In the drawing, a reference symbol AP represents a universal AC connector for AC 100 V to 300 V, and MP1 and MP2 are electric electrophoresis outputs points which are connected to platinum electrodes or the like members. A reference symbol G designates a carrier for electrophoresis such as agarose gel or polyacrylamide gel which is generally used.

Let us assume that the change-over switch 3 is set in a condition where it connects the half-wave rectified wave generator 1 to the polarity switching relay 4 and that the polarity switching relay 4 is connected so as to set the MP 1 and MP2 in the positive direction and in the negative direction respectively.

The AP connectors are connected to a universal AC electric outlet such as a domestic plug socket. A universal AC current is supplied through the fuse 7 to the half-wave rectified wave generator 1, the full-wave rectified wave generator 2 and the control means 5.

The input universal AC current is converted by the half-wave rectified wave generator 1 into half-wave rectified wave (FIG. 3a), and supplied through a driving section including the change-over switch 3 and the polarity switching relay 4 to the electrophoresis output points MP1 and MP2.

Since the change-over switch 3 and the polarity switching relay 4 have very low resistance when turned on, the half-wave rectified wave generated by the half-wave rectified wave generator 1 is efficiently supplied to the electrophoresis output points MP1 and MP2.

When a button switch or a similar member is depressed, an input is generated as the external input IN, and the input means 6 generates a control signal such as a DC pulse on the basis of this input, At the same time if a controll signal is generated to a switch section selected as a destination, the change-over switch 3 is turned to connect the full-wave rectified wave generator 2 to the polarity switching relay 4 for outputting the full-wave rectified wave (FIG. 3b) to electrophoresis output terminals MP1 and MP2.

When an external input 1 generates an input for changing polarities of the polarity switching relay 4, input means 6 outputs a similar signal to the polarity switching relay 4, thereby providing rectified outputs to the electrophoresis output points MP2 and MP1 in positive and negative directions respectively.

The electric controller according to the present invention described above allows to obtain electrophoresis outputs which are effective like the conventional outputs but operates very safely since it operates at low voltage levels obtained by controlling the universal AC voltage with the control means 5, etc., and can easily permit connection of timers and other functions. Further, the electric controller can prevent directly manipulated members from being deteriorated even when they are manipulated roughly by users, and allows the switching section to be controlled safely and stably since the switching section which directly prepares electrophoresis electric outputs is kept under indirect electric control.

[First Embodiment]

Figure 2:
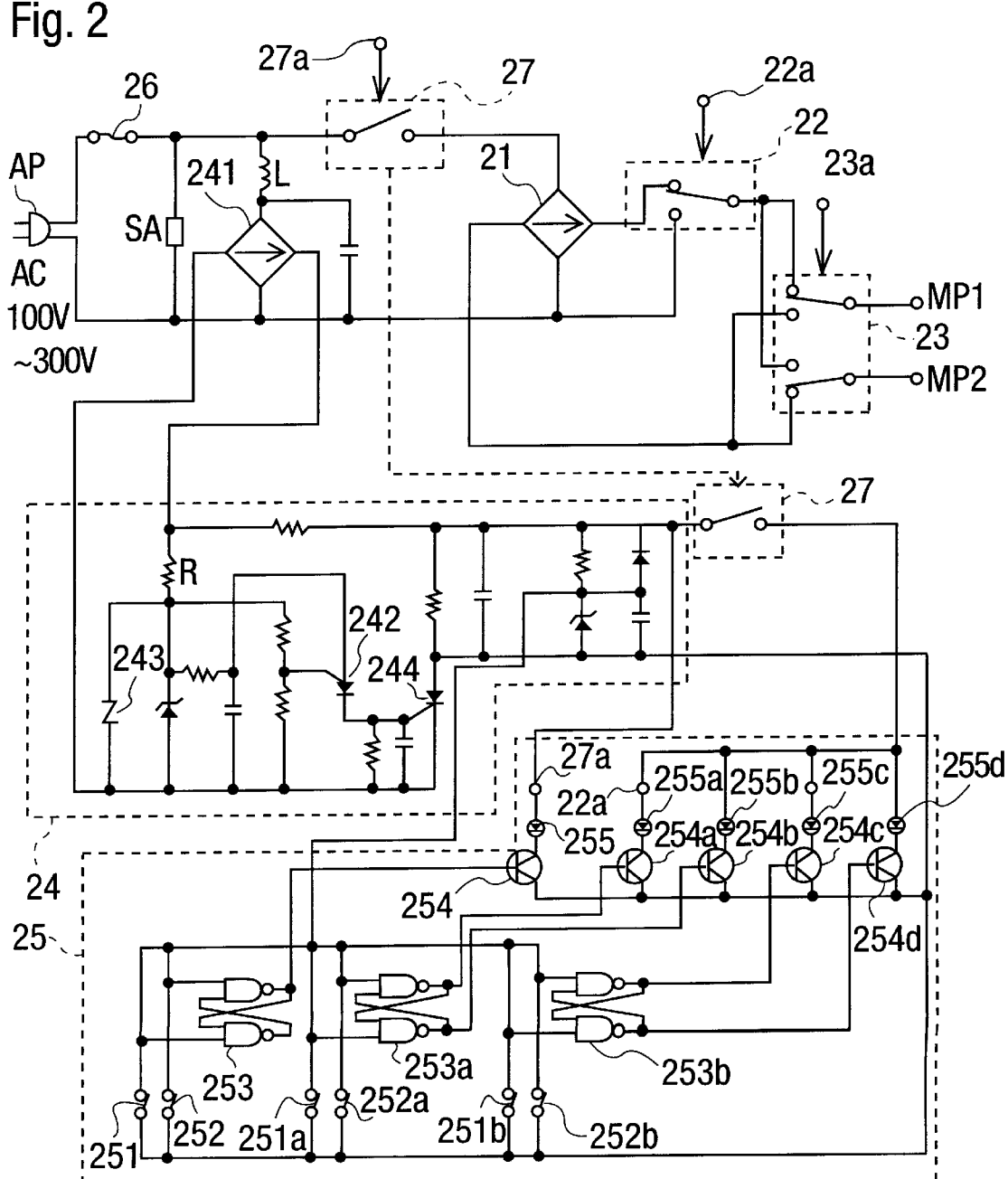
FIG. 2 is a circuit diagram illustrating another embodiment of the simplified electrophoresis apparatus according to the present invention.
Figure 5:
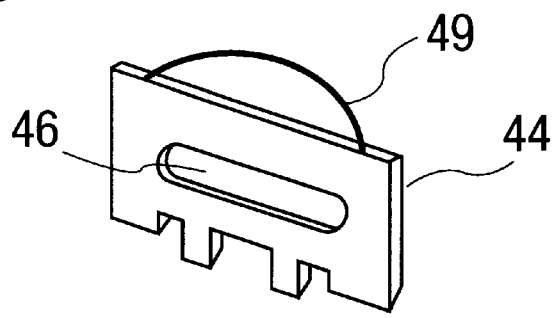
FIG. 5 is a perspective view illustrating a shutter for the electric controller.

Now, a more concrete embodiment will be described with reference to FIG. 2.

A reference numeral 21 represents a rectifier which is composed of a diode bridge and provides a half-wave rectified or full-wave rectified output. A relay 22 performs a switching operation with a signal from an input terminal 22a. A polarity switching relay 23 performs a switching operation with an electric signal from an input terminal 23a. Two output switching relay 27 provides and intercepts an output to and from electrophoresis output means and input means in accordance with an input fed into an input point 27a.

A voltage control circuit 24 prepares a low DC voltage and comprises a circuit which establishes an electrically shielded condition when an overcurrent or overvoltage is input.

A reference numeral 241 designates a rectifier which has a composition similar to that of the rectifier 21 described above.

A reference numeral PUT (Programmable Unijunction Transistor) 242 denotes a negative resistance element and sidac, also known as a Bi-Directional Diode Thyristor, 243 is also a negative resistance element. A reference numeral 244 represents a thyristor. A reference symbol SA designates a surge absorber which serves for absorbing a counterelectromotive force of an inductor L.

An input control means 25 comprises a manual control switch and is used for outputting a signal which is generated by depressing this switch to the relays 22, 23 and 27. In this embodiment, 251, 252, 251a, 251b, 252a and 252b for outputting control signals to the change-over switch 3 are, for example, membrane-like depressing switches which are electrically connected when depressed and electrically disconnected when released. 253, 253a and 253b are flip-flop circuits which are composed of combinations of NAND circuits.

254, 254a, 254b, 254c and 254d are switching transistors which are turned on and off by outputs from the flip-flop circuits disposed at the preceding stage.

255, 255a, 255b, 255c and 255d are LEDs for displaying circuit operations.

Now, operations of this embodiment will be described below.

The input terminals AP are connected to a universal AC power source of AC 100 V for supplying the universal AC current to the control circuit 24 and the relay 27.

In the control circuit 24, the universal AC current is input into a rectifier 241 and full-wave rectified. PUT 242 operates as a portion of a circuitry like an oscillator circuit which receives a full-wave rectified wave and outputs a trigger pulse to a gate of thyristor 244 at a rising time of the wave. On the basis of the trigger pulse, etc., the thyristor 244 turns on and off for controlling phases of the full-wave rectified wave, thereby lowering a voltage to be supplied to the input means 25. The voltage is lowered, for example, at a ratio of 1/3 to 1/4, or to approximately 40 V when an input voltage is 120 V, though it may be lowered at an optional ratio dependently on ratings for parts composing the input means 25.

When output of the flip-flop circuit 253 is set at a low level in the input means 25, the output of the flip-flop circuit 253 is set at a high level and the switching transistor 254 is turned on by depressing the switch 251. The LED 255 glows and the current is supplied to a control input point 27a of the relay 27, thereby turning on the relay 27.

The flip-flop circuit 253 is kept in this condition until the switch 252 is depressed. When the switch 252 is depressed, the output of the flip-flop circuit 253 is set at the low level and the LED 255 goes out, thereby turning off the relay 27.

When the relay 27 is turned on, the universal AC current is supplied to the rectifier 21, the rectifier 21 outputs both the full-wave rectified wave and half-wave rectified wave, and the relay 22 switches electric connections between these two outputs and the polarity switching relay 23 with an input to the relay control input point 22a.

Further, the relay 23 functions to switch polarities of the output of the rectifier connected by way of the relay 22 and provide the output to the electrophoresis output terminals MP1 and MP2. First, the relay 23 is connected to provide a rectified output which sets MP1 and MP2 in the positive direction and the negative directions respectively. In this condition, a half-wave rectified output in the positive direction and a half-wave rectified output in the negative direction are provided to the electrophoresis output terminals MP1 and MP2 respectively. In this condition, the switching transistor 254a of the flip-flop circuit 253a is turned off for providing the output at the low level and the switching transistor 254b is turned on for providing the output at the high level from the opposite side. The LED 255b glows to indicate that the half-wave rectified output is provided.

When the switch 251a is depressed, the output of the flip-flop circuit 253a is inverted to turn on the transistor 254a and glow the LED 255a. On the other hand, the LED 255b goes out and the current is supplied to the relay control input terminal 22a and selected conditions of the relays are switched, whereby the full-wave rectified output is provided to set the electrophoresis output terminals MP1 and MP2 in the positive direction and the negative direction respectively. When the switch 252a is depressed, the output of the flip-flop circuit 253a is inverted once again and the current is not supplied any longer to the relay control input terminal 22a, thereby changing over the relay 22.

The switching transistor 254c for the flip-flop circuit 253b is turned off to provide an output at a low level, the switching transistor 254b is turned on to provide an output at a high level on the opposite side and the LED 255d glows to indicate that the MP1 is providing output in the positive direction.

When the switch 251b is depressed, the output of the flip-flop circuit 253b is inverted, the transistor 254c is turned on and the LED 255c glows, whereas the LED 255d goes out, the current is supplied to the relay control input terminal 23a, the polarity selecting condition of the relay 23 is changed over, and the full-wave rectified output is provided to set the electrophoresis output terminals MP1 and MP2 in the negative direction and the positive direction respectively.

When the switch 252a is depressed, the output of the flip-flop circuit 253a is inverted once again and the current supply to the relay control terminal 22a is stopped, thereby changing over the relay 22.

Then, description will be made of operations which are performed in occurrence of an overcurrent or an abnormal voltage due to an abnormality. When an overcurrent is supplied to a main circuit around the rectifier 21, the fuse 26 is heated and blown, thereby opening the main circuit and stopping the electrophoresis output.

When an overcurrent or an abnormal voltage is generated due to injury of a resistor R in the control circuit, a bypass means is formed by the thydac 243, which is turned on to supply an overcurrent to the fuse 26, thereby opening the circuit.

Since the electric controller described concretely as the embodiment (except the electrophoresis cell) is composed of parts most of which consume small amounts of electric energy and configured as universal chips, it can be assembled so as be accommodated in a housing measuring approximately 40 cm deep by 80 cm wide by 26 com high, for example, or configured compact and light in weight.

[Second Embodiment]

An electric controller A has an input section 40, a polarity switching relay 41, rectified wave selector switch 42, a power input switch 43 and an output terminal which is configured as a socket and disposed in a housing of the electric controller A. A convex terminal disposed on an electrophoresis cell unit B is inserted into the output terminal for electrically connecting the electric controller to the electrophoresis cell unit B and has an insert portion 45 which is always closed with a shutter 44 urged downward in the housing of the electric controller A by a spring 49. When the electric controller A is set in the electrophoresis cell unit B, the shutter 44 is pushed from downside so that an elongated slot 46 formed in the shutter 44 is coincident with the insert portion 45 of the shutter 44 to open the elongated slot.

As a mechanism for pushing up the shutter 44, a convex rib is formed on the electrophoresis cell unit B in a direction for inserting the electrophoresis cell unit B at a setting location for the electric controller A and the electric controller is configured to allow the shutter 44 to be pushed up by this convex rib.

Further, the electrophoresis apparatus according to the present invention is configured, for security of use, so as not to allow electrical connection between the electrophoresis cell unit B and the electric controller A so long as the electrophoresis cell unit is not protected with a cover C.

For composing a security mechanism in this embodiment, a terminal on the electrophoresis cell unit B is not configured as the convex terminal described above but the electric controller has a socket which is configured so as not to be electrically connected to the electrophoresis cell unit B when it is set in the cell unit and a convex terminals 47 is formed on an electrophoresis cell cover C as a conductive connector between electrodes so that one of the convex terminals 47 is plugged into the socket of the electric controller A and the other of the convex terminals 47 is brought into contact with a terminal of the electrophoresis cell unit B for establishing electrical connection.

Figure 6:
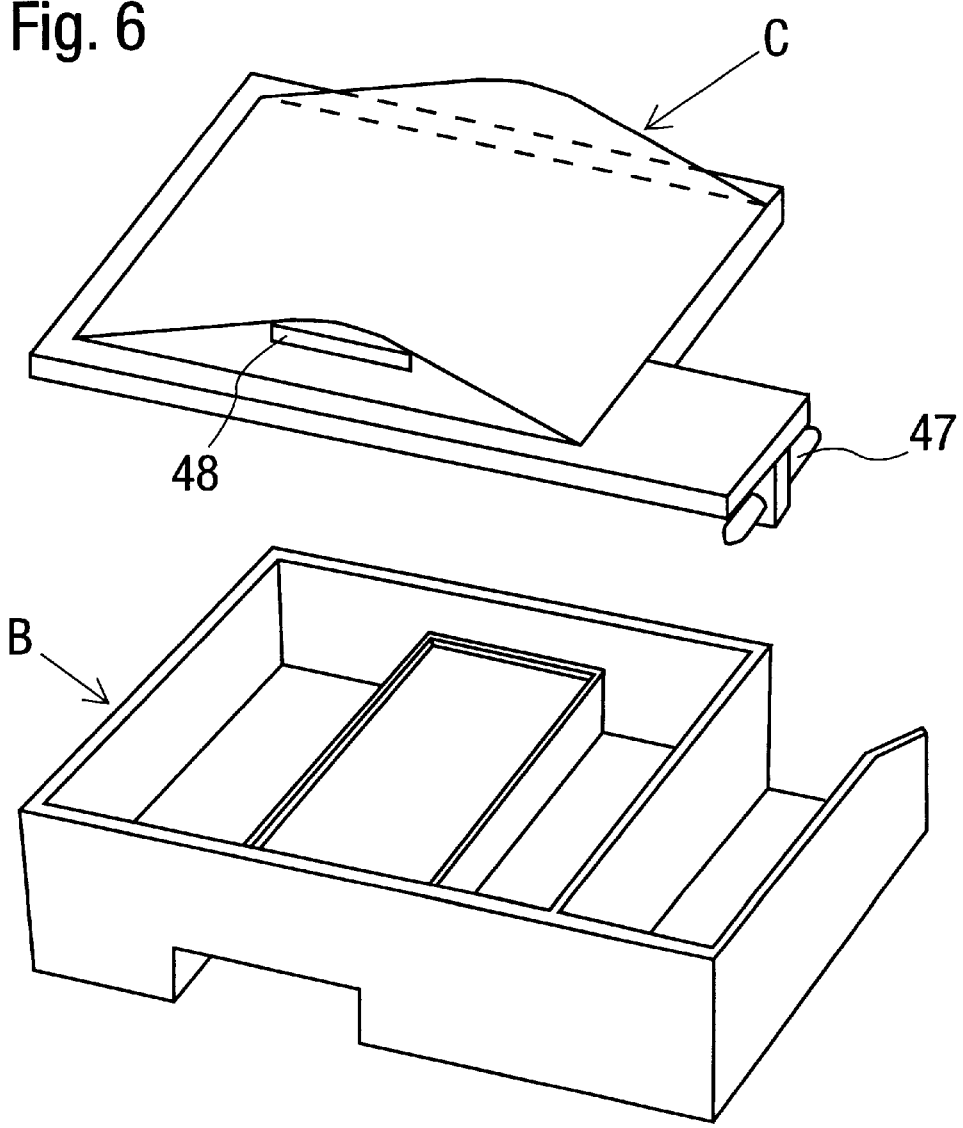
FIG. 6 is a perspective view of a cover.

Accordingly, an electric current cannot be supplied to the electrophoresis cell unit so long as it is not protected with the cover C. Further, the cover C is configured so as to have a semicylindrical or semispherical form (FIG. 6) so that dews produced from an electrophoresis liquid which is normally heated to 40° C. can be removed along a slanted surface. Furthermore, a ventilation slot 48 is formed in a side surface and the cover C is engaged with the electrophoresis cell unit B by way of convexities formed at an adequate intervals so as to form air vents or a ventilation structure between these members, whereby electrophoresis processes can be observed free from hindrance due to water drops.

Industrial Applicability

As understood from the foregoing description, the present invention makes it possible to obtain an electrophoresis apparatus which is capable of providing excellent electrophoresis outputs, can be configured compact and light in weight since the apparatus can be composed of elements having sizes of several millimeters without requiring no special parts, and operates stably with a safe interface which is constituted by indirectly driving and controlling electrically and mechanically, a controller for controlling a user's interface and electrophoresis. The control is also very safe since it is performed by control means at low. voltages obtained by adjusting a universal AC voltage.

What is claimed is:

1. An electrophoresis apparatus for an electrophoresis cell, the electrophoresis apparatus comprising:

an AC connector for connecting to an AC power source;

a rectifier arrangement connected to said AC connector for rectifying electricity from said AC connector and generating a rectified electric output;

a driving section for receiving said rectified electric output from said rectifier arrangement and for applying said rectified electric output to the electrophoresis cell, said driving section maintaining a voltage magnitude and a current magnitude of said rectified electric output substantially constant from said rectifier arrangement to the electrophoresis cell.

2. A electrophoresis apparatus in accordance with claim 1, wherein:
said driving section does not include a transformer for transforming said rectified electric output.

3. A electrophoresis apparatus in accordance with claim 1, further comprising:
a switching means for interrupting an electrical connection between said AC connector and said rectifier arrangement during an abnormal electrical output of said driving section.

4. A electrophoresis apparatus in accordance with claim 3, wherein:
said switching means opens said electrical connection upon an over current condition.

5. A electrophoresis apparatus in accordance with claim 3, wherein:
said switching means is one of a fuse and a circuit breaker.

6. A electrophoresis apparatus in accordance with claim 3, further comprising:
input control means for controlling said driving section based on an external input;
voltage control means for receiving said rectified electric output and delivering a control voltage to said input control means, said voltage control means including a bypass means for activating said switching means during an abnormal electrical output to said input control means.

7. A electrophoresis apparatus in accordance with claim 6, wherein:
said bypass means activates said switching means upon an over current condition in said input control means.

8. A electrophoresis apparatus in accordance with claim 6, wherein:
said bypass means includes a thydac for generating an over current condition at said switching means.

9. A electrophoresis apparatus in accordance with claim 1, further comprising:
input control means for controlling said driving section based on an external input, a connection between said driving section and said input control means includes an electrically insulated switching device.

10. A electrophoresis apparatus in accordance with claim 1, wherein:
said rectifier arrangement includes a full wave rectifier and a half wave rectifier.

11. A electrophoresis apparatus in accordance with claim 10, wherein:
said driving section includes a change over switch for switching between receiving said rectified electric output from said full wave rectifier and said half wave rectifier.

12. A electrophoresis apparatus in accordance with claim 1, wherein:
said driving section includes a polarity switch for switching a polarity of said rectified electrical output delivered to the electrophoresis cell.

13. A electrophoresis apparatus in accordance with claim 1, further comprising:
input control means for controlling said driving section based on an external input;
voltage control means for receiving said rectified electric output and lowering said rectified electrical output to a control voltage, said voltage control means delivering said control voltage to said input control means.

14. A electrophoresis apparatus in accordance with claim 13, wherein:
said voltage control means includes two negative resistance elements to lower said rectified electric output.

15. A electrophoresis apparatus in accordance with claim 14, wherein:
one of said negative resistance elements is a Programmable Unijunction Transistor (PUT) and another of said negative resistance elements is a SIDAC.

16. A electrophoresis apparatus in accordance with claim 13, further comprising:
a switching means for interrupting an electrical connection between said AC connector and said rectifier arrangement during an abnormal electrical output of said driving section;
said voltage control means includes a bypass means for activating said switching means during an over current condition in said input control means.

17. A electrophoresis apparatus in accordance with claim 1, wherein:
said AC connector connects to a commercial AC power source with a voltage between 100 through 300 volts.

18. A electrophoresis apparatus in accordance with claim 1, wherein:
said AC connector connects to a utility main line AC power source.

19. A electrophoresis apparatus in accordance with claim 1, wherein:
said AC connector connects to a utility main line AC power source between 100 and 300 volts and delivers the electricity from the power source to said rectifier arrangement while maintaining a voltage magnitude and a current magnitude of the power source electricity substantially constant.

* * * * *